United States Patent [19]

Geddes et al.

[11] 4,387,714

[45] Jun. 14, 1983

[54] ELECTROSURGICAL DISPERSIVE ELECTRODE

[75] Inventors: Leslie A. Geddes; Joe D. Bourland, both of West Lafayette; John A. Pearce, Battleground, all of Ind.

[73] Assignee: Purdue Research Foundation, West Lafayette, Ind.

[21] Appl. No.: 263,212

[22] Filed: May 13, 1981

[51] Int. Cl.³ .............................................. A61B 17/39
[52] U.S. Cl. ................................ 128/303.13; 128/798
[58] Field of Search ...................... 128/303.13, 303.14, 128/783, 798, 802, 804

[56] References Cited

U.S. PATENT DOCUMENTS

| | | | |
|---|---|---|---|
| 3,848,600 | 11/1974 | Patrick, Jr. et al. | 128/783 X |
| 4,121,592 | 10/1978 | Whalley | 128/804 X |
| 4,166,465 | 9/1979 | Esty et al. | 128/303.13 |
| 4,188,927 | 2/1980 | Harris | 128/303.14 |
| 4,303,073 | 12/1981 | Archibald | 128/303.13 |
| 4,304,235 | 12/1981 | Kaufman | 128/303.13 |

*Primary Examiner*—Lee S. Cohen
*Attorney, Agent, or Firm*—Robert E. Harris; John R. Nesbitt

[57] ABSTRACT

An electrosurgical dispersive electrode is disclosed that is useful in conjunction with an electrosurgical unit to establish capacitive-coupling with the skin of a patient receiving therapeutic signals from the electrosurgical unit. The electrode includes a metallic plate electrically connectable with the electrosurgical unit to establish a return current path thereto, an insulator engaging the inner (patient) side of the metallic plate to prevent ohmic contact by the plate with the skin of the patient, and a conductive adhesive gel at the outer (patient) side of the insulator so as to be positioned between the insulator and the skin of a patient to bring the skin uniformly in contact with the gel conductor and thereby reduce the impedance, normally associated with capacitively-coupled dispersive electrodes, while retaining uniform temperature distribution.

4 Claims, 3 Drawing Figures

ELECTROSURGICAL DISPERSIVE ELECTRODE

Government Rights

The invention described herein was made in the course of work under a grant or award from the Department of Health, Education, and Welfare.

FIELD OF THE INVENTION

This invention relates to a dispersive electrode and, more particularly, relates to a hybrid capacitively-coupled, electrosurgical dispersive electrode.

BACKGROUND OF THE INVENTION

Electrosurgical dispersive electrodes are now known, and such electrodes are now utilized to provide a return current path to an electrosurgical generator from a patient receiving therapeutic signals from the generator through an active electrode in contact with the patient.

Electrosurgical dispersive electrodes now known and/or utilized may be either for single-use (i.e., disposable) or multiple-use (i.e., re-usable), and may be typified as either resistive-contact or capacitive-contact electrodes.

Resistive-contact electrodes now known and/or utilized employ a bare metallic electrode in contact with the skin or an electrolytically conductive gel between and in engagement with a metallic electrode and the skin surface. Because of the characteristics of the resulting electrical boundary conditions, the current is not evenly distributed over the surface of the electrode, with the current density being much higher at the edges than at the center of the electrode. This results in a hot perimeter, and a patient is more likely to receive a burn at the edge of the electrode because of the uneven current distribution. Resistive-contact electrodes have an advantage, however, in that the electrolytic gel provides a low impedance contact. Moreover, the electrolytic gel at room temperature cools the skin slightly when the electrode is applied and this results in lessening of the skin-temperature rise.

A resistive-contact type of electrode used as an electro-surgical dispersive electrode is shown, by way of example, in U.S. Pat. Nos. 4,088,133 and 3,848,600.

Presently known and/or utilized capacitive-contact electrode, on the other hand, have a thin dielectric film between the metallic electrode and the skin. The skin forms one "plate" of a capacitor, while the metallic electrode forms the other plate to thus establish capacitive contact. The electrical boundary conditions for capacitive-contact electrodes are such that, if ideal capacitive contact is made, the current is necessarily uniformly distributed over the electrode surface, and there is no hot perimeter. A further advantage of capacitive electrodes is that they are more convenient to store and apply than resistive-contact electrodes.

Known capacitive-contact electrodes, however, have disadvantages, including: lack of a conducting gel which cools (thus the final temperature may be higher than with gelled electrodes); requirement of use of the skin as a "plate" (the skin also has dielectric properties and is an unpredictable participant in the capacitive coupling process); difficulty of uniform capacitive electrode-skin separation (uniform contact is not easily achievable in practice and buckling of the electrode causes hot spots); and creation of slightly high impedance (the capacitive electrode exhibits a slightly higher impedance than gel-contact electrodes).

Capacitive-contact electrodes used as electrosurgical dispersive electrodes are shown, by way of example, in U.S. Pat. Nos. 4,200,104, 4,188,927, and 4,166,465.

SUMMARY OF THE INVENTION

This invention provides an improved electrosurgical dispersive electrode that is capacitively-coupled to obtain the advantages of the capacitive-contact type of electrode and utilizes a conductive electrolyte common to the resistive-contact type of electrode to also obtain the advantages of this type of electrode. The hybrid electrode thus achieved substantially eliminates the undesirable hot perimeter commonly found in the resistive-contact type of electrode while also substantially reducing the high impedance found in the capacitive-contact type of electrode, the foregoing being accomplished through use of a hybrid capacitive-contact type of electrode that includes a layer of conductive electrolyte, which can be an adhesive.

It is therefore an object of this invention to provide an improved dispersive electrode for use with an electrosurgical generator.

It is another object of this invention to provide an improved dispersive electrode that is a hybrid capacitive-contact electrode.

It is yet another object of this invention to provide an improved dispersive electrode that is capacitively-coupled and yet includes a layer of conductive electrolyte.

It is still another object of this invention to provide an improved capacitively-coupled, dispersive electrode having an adhesive layer of conductive electrolyte.

With these and other objects in view, which will become apparent to one skilled in the art as the description proceeds, this invention resides in the novel construction, combination, and arrangement of parts substantially as hereinafter described, and more particularly defined by the appended claims, it being understood that such changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which.

DESCRIPTION OF THE INVENTION

Figure 1:
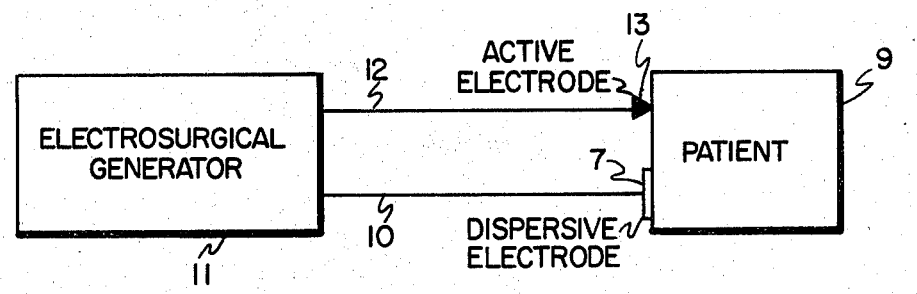
FIG. 1 is a block and schematic diagram illustrating use of the dispersive electrode of this invention in conjunction with an electrosurgical generator for providing a return current path from the patient to the generator.

As shown in FIG. 1, dispersive electrode 7 is placed in non-invasive engagement with the skin of a patient 9 to serve as an indifferent (dispersive or ground plate) electrode and hence to provide a return current path through lead 10 for therapeutic signals (commonly RF signals) generated by electrosurgical generator 11 and coupled to the patient through lead 12 and active electrode 13. As is well known, such signals may be utilized in surgical procedures for cutting, coagulation and/or fulguration purposes.

Figure 2:
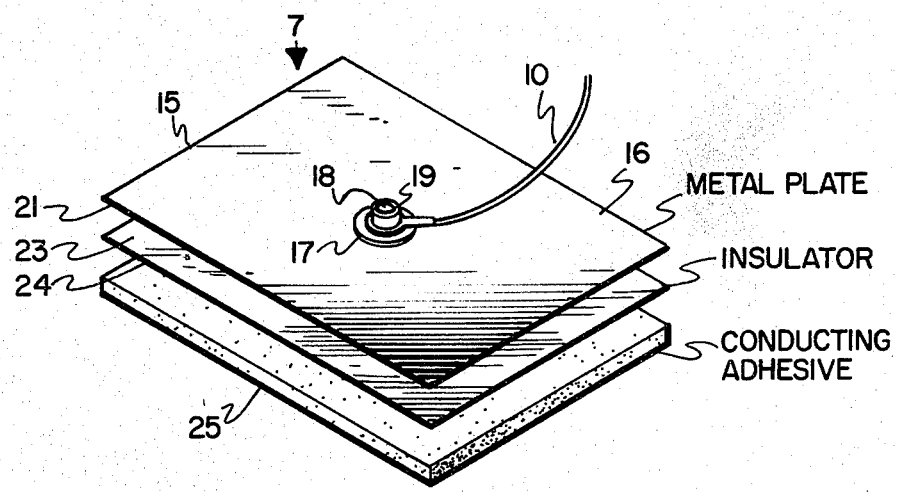
FIG. 2 is an exploded perspective view of the dispersive electrode of this invention.
Figure 3:
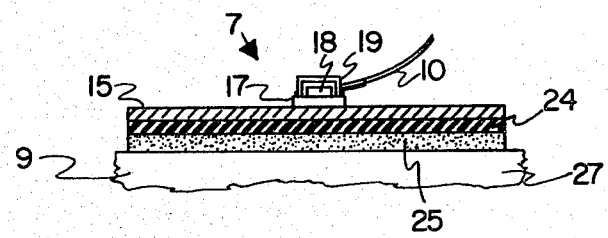
FIG. 3 is a side view of the dispersive electrode as shown in FIG. 2.

Dispersive electrode 7 of this invention is a hybrid capacitively-coupled type of electrosurgical dispersive electrode that incorporates the best features of both the resistive-contact and capacitive-contact types of electrodes. Electrode 7, as shown in FIGS. 2 and 3, includes a metallic plate 15 the upper side 16 of which has a fastener 17 affixed thereto in conventional fashion with fastener 17 having an upstanding socket 18 thereon to receive a snap fastener 19 attached to return lead 10 leading to electrosurgical generator 11. The lower side 21 of plate 15 is in engagement with the upper side 23 of insulator 24, while the lower side of insulator 24 has a conductive adhesive 25 thereon.

Plate 15 and insulator 24 may be of commonly known conductive and non-conductive materials, respectively, and may be dimensioned as needed for a particular application with the thickness of each being normal for the capacitive-contact type of electrode as now known. In addition, the particular manner of fastening return lead 10 to metallic plate 15 may be varied as would be obvious to one skilled in the art, and metallic plate 15 may be glued or otherwise bonded to insulator 24 as would also be obvious to one skilled in the art.

Plate 15 thus serves as one conductor plate, while the other conductor plate needed to form a parallel-plate capacitor is provided by the subsurface skin layer 27 of a patient 9 when the hybrid capacitively-coupled dispersive electrode 7 of this invention is in engagement with the skin of such a patient as illustrated in FIG. 3. When so positioned, insulator 24 maintains uniform spacing between the "plates" of the thus formed parallel-plate capacitor. In addition, while the dry surface skin layer (i.e., the barrier layer) also has primarily dielectric properties, the conductive adhesive layer 25 makes the skin conductive.

The electrical and heat-transfer characteristics of capacitively-coupled electrodes are very different from those of the more traditional resistive-contact (i.e., gel-pad and gelled metal) dispersive electrodes, and, consequently, their normal performance is also quite different (see "The Characteristics of Capacitive Electrosurgical Dispersive Electrodes" by A. J. Pearce and L. A. Geddes, AAMI 15th Annual Meeting, Apr. 13–17, 1980, San Francisco, Calif., page 162).

Total current density is the sum of the conductive and displacement components. The current in the dielectric is displacement current only, since it is non-conductive. In the underlying tissue, conduction current dominates the displacement current at the frequencies normally associated with electrosurgical generators. This has two important consequences—insignificant power is dissipated in the dielectric layers, and the ratio of resistivities at the interface is such that the field vectors must be perpendicular to the boundary.

These conditions are in contrast with the resistive-contact types in that resistive-contact electrodes do dissipate some (though usually nominal) power in the gel, and they do have significant bends in the field lines at the interface.

As a result, with ideal capacitive contact, the current is uniformly distributed over the electrode surface, while with resistive-contact electrodes the current density is higher at the edges than at the center of the electrode (see K. M. Overmayer, A. J. Pearce and D. P. DeWitt, Trans. ASME, J. Biomech. Engr., Volume 101, note 1, pages 66–72, February, 1979).

Even though the current is more uniform when utilizing a capacitively-coupled electrode, the temperature rise heretofore encountered with such electrodes has been found to be normally higher than for a comparable resistive-contact type of electrode because the large mass of room temperature gel normally cools the skin on application while also wetting the barrier layer to promote good resistive contact. In addition, as brought out hereinabove, the capacitively-coupled electrode now known exhibits high impedance.

In the electrode of this invention, it has been found that through the addition of a conductive adhesive gel 25 between and in engagement with insulator 24 and the skin of a patient, the disadvantages of the capacitively-coupled electrode are substantially eliminated, while retaining its advantages and in addition, the advantages of the resistive-contact electrode are achieved while substantially eliminating the disadvantages of this type of electrode.

In particular, the two undesirable features of existing electrodes, namely the hot perimeter of resistive-contact electrodes and the high impedance and higher skin temperature of capacitive-contact electrodes are removed with the hybrid electrode of this invention.

As brought out hereinabove, the hybrid capacitive electrode of this invention consists of a capacitively-coupled electrode utilized in conjunction with a conductive adhesive gel. This results in no ohmic contact between the electrode and the skin of a user, and the presence of the conducting electrolyte brings the skin uniformly into contact with the dielectric of the capacitively-coupled electrode, thereby reducing the impedance dramatically, while at the same time, retaining the uniform temperature distribution of capacitively-coupled electrodes.

In view of the foregoing, it should be realized that this invention provides an improved electrode that is particularly useful as an electrosurgical dispersive electrode.

What is claimed is:

1. A hybrid capacitively-conductively coupled dispersive electrode, comprising:

an electrically conductive element adapted to be electrically connected with an electrosurgical unit capable of providing a therapeutic signal to a patient, said conductive element having an inner portion;

an insulating element having inner and outer portions with said outer portion of said insulating element engaging and covering said inner portion of said conductive element to prevent ohmic contact of said inner portion of said conductive element with the skin of a patient during normal use of said electrode; and an electrically conductive adhesive having inner and outer portions with said outer portion of said adhesive engaging said inner portion of said insulating element and said inner portion of said adhesive being formed so as to be engageable with the skin of a patient receiving said therapeutic signals from said electrosurgical unit to effectively enable uniform contact of said skin with said conductive adhesive to provide electrolytic communication through the skin to the patient and to establish capacitive-coupling between said conductive element and said conductive adhesive when said inner portion of said adhesive is engaged with said skin with said established capacitive-conductive coupling providing low impedance while retaining the uniform temperature distribution of capacitively-coupled electrodes.

2. The dispersive electrode of claim 1 wherein said conductive element is a metallic plate.

3. The dispersive electrode of claim 1 wherein said conductive adhesive covers at least the entire inner portion of said insulating element.

4. A hybrid capacitively-conductively coupled dispersive electrode, comprising:

a metallic plate adapted to be connected with an electrosurgical unit capable of providing a therapeutic signal to a patient, said plate having an inner side;

an insulating sheet having inner and outer sides with the outer side of said insulating sheet engaging said inner side of said metallic plate and substantially entirely covering the same; and a conductive adhesive gel engaging and substantially entirely covering said inner side of said insulating sheet, said gel also being engageable with the skin of a patient receiving said therapeutic signal from said electrosurgical unit to effectively enable uniform contact of said skin with said conductive adhesive gel to provide electrolytic communication through the skin to the patient and to establish capacitive-coupling between said metallic plate and said conductive adhesive gel when said gel is in engagement with the skin of the patient with said established capacitive-conductive coupling providing low impedance while retaining the uniform temperature distribution of capacitively-coupled electrodes.

* * * * *